(12) United States Patent
Khan

(10) Patent No.: US 11,898,051 B1
(45) Date of Patent: Feb. 13, 2024

(54) SILICONE SEPTUM COATING

(71) Applicant: Becton, Dickinson and Company, Franklin Lakes, NJ (US)

(72) Inventor: Azhar Khan, Bluffdale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/982,319

(22) Filed: Nov. 7, 2022

(51) Int. Cl.
- *A61L 29/02* (2006.01)
- *B65D 59/02* (2006.01)
- *C09D 151/08* (2006.01)
- *A61L 29/10* (2006.01)

(52) U.S. Cl.
CPC .......... *C09D 151/085* (2013.01); *A61L 29/02* (2013.01); *A61L 29/103* (2013.01)

(58) Field of Classification Search
CPC ................................ A61L 29/02; B26D 59/02
USPC ..................................................... 607/167.02
See application file for complete search history.

(56) References Cited

U.S. PATENT DOCUMENTS

| | | | |
|---|---|---|---|
| 4,066,183 A | 1/1978 | Armstrong | |
| 8,469,928 B2 * | 6/2013 | Stout | A61M 39/0208 604/167.04 |
| 2003/0148030 A1 * | 8/2003 | Vernon, Jr. | C08J 7/048 427/255.28 |
| 2006/0051392 A1 * | 3/2006 | Heruth | A61L 27/34 424/423 |
| 2009/0264572 A1 * | 10/2009 | Liao | C09D 7/67 524/506 |
| 2010/0186740 A1 * | 7/2010 | Lewis | A61B 17/00 604/265 |
| 2011/0160663 A1 * | 6/2011 | Stout | A61M 25/0693 604/122 |
| 2015/0202422 A1 * | 7/2015 | Ma | A61M 39/0693 604/167.02 |
| 2017/0175263 A1 * | 6/2017 | Yamamoto | C23C 16/045 |

* cited by examiner

*Primary Examiner* — Cachet I Proctor
(74) *Attorney, Agent, or Firm* — Kirton McConkie; Whitney Blair; Kevin Stinger

(57) ABSTRACT

A silicone septum having a surface coating. The coated silicone septum may be incorporated in an intravenous catheter assembly. The coating reduces static charge among a plurality of vibrating silicone septa during manufacture of the intravenous catheter assembly. The surface coating includes a coating agent selected from a bicarbonate salt and a siloxane polyalkyleneoxide copolymer. The bicarbonate salt may be an alkali metal bicarbonate. The siloxane polyalkyleneoxide copolymer may include copolymer groups selected from ethyleneoxide, octamethylcyclotetrasiloxane, and mixtures thereof. The silicon septum may be coated by contacting an exterior surface of the silicone septum with a coating solution of a solvent and the coating agent for at least 5 minutes. The coating agent has a concentration in the solvent greater than 1 wt. %. Excess coating solution is removed from the exterior surface of the silicone septum. The exterior surface is dried to remove the solvent, forming the surface coating.

13 Claims, 2 Drawing Sheets

SILICONE SEPTUM COATING

BACKGROUND

This disclosure relates to coatings for a silicone septum used with intravenous (IV) catheter assemblies. The disclosure further relates to methods of coating a silicone septum. The silicone septum coatings disclosed herein may reduce static charge among a plurality of vibrating silicone septa and may facilitate manufacture of intravenous catheter assemblies.

Intravenous catheter assemblies are among various types of vascular access devices. Intravenous catheter assemblies disclosed herein include a catheter coupled to a catheter adapter.

A septum is positioned within a lumen of the intravenous catheter assembly to prevent or limit flow of a fluid through the catheter adapter. The septum generally includes a flexible or semi-flexible material that is compatible with exposure to blood, medicaments, and other fluids commonly encountered during infusion procedures. The septum may comprise a silicone material. A groove may be provided on an inner surface of the catheter adapter, wherein the septum is seated within the groove. As such, the position of the septum within the catheter adapter is maintained.

During manufacture of the intravenous catheter assembly, plural silicone septa are deposited within a vibrating feeder bowl. The vibration separates and moves septa through feed lines where they are ultimately taken and placed into the catheter adapter. The vibration also causes septa to bounce and rub against each other, creating static charge. Under these conditions, the static charge causes septa to stick to each other and fail to move through the feedlines at a required manufacturing speed.

There is a need to prevent or reduce static charge among a plurality of vibrating silicone septa so that the septa do not stick to each other and so that the septa will move through manufacturing feedlines at a suitable feed rate, thereby facilitating the manufacture of intravenous catheter assemblies.

SUMMARY

The present disclosure relates generally to a coating for a silicone septum used in a vascular access device, such as an intravenous catheter assembly. The present disclosure relates to an intravenous catheter assembly comprising a coated silicone septum disclosed herein. The present disclosure further relates to a method for coating a silicone septum. The present disclosure relates to a method of reducing static charge among a plurality of vibrating silicone septa by coating the silicon septa as disclosed herein.

One general aspect of the disclosed invention includes a silicone septum comprising a surface coating. The surface coating comprises a coating agent selected from a bicarbonate salt and a siloxane polyalkyleneoxide copolymer.

Non-limiting examples of the bicarbonate salt include alkali metal bicarbonate salts, such as lithium bicarbonate, sodium bicarbonate, and potassium bicarbonate.

The siloxane polyalkyleneoxide copolymer may comprise copolymer groups selected from ethyleneoxide, octamethylcyclotetrasiloxane, and mixtures thereof. An example of this type of siloxane compound is L-8620 surfactant available from Momentive performance Materials Inc.

Another general aspect of the disclosed invention includes an intravenous catheter assembly comprising a coated silicone septum as disclosed herein.

One general aspect of the disclosed invention includes a method of coating a silicone septum. The method includes contacting an exterior surface of the silicone septum with a coating solution. The coating solution may include a solvent and a coating agent. The coating agent is selected from a bicarbonate salt and a siloxane polyalkyleneoxide copolymer. The coating agent has a concentration in the solvent greater than 1 wt. %.

In one embodiment of the method, the exterior surface of the silicone septum is contacted with the coating solution for at least 5 minutes.

The method also includes removing excess coating solution from the exterior surface of the silicone septum.

The method also includes drying the exterior surface of the silicone septum.

In one non-limiting embodiment of the method, the coating agent has a concentration in the solvent in the range from 1 wt. % to 10 wt. %. In another non-limiting embodiment, the coating agent has a concentration in the solvent in the range from 1 wt. % to 5 wt. %. In another non-limiting embodiment, the coating agent has a concentration in the solvent in the range from 2 wt. % to 4 wt. %.

In one embodiment, the solvent is water.

In an embodiment, the coating agent comprises sodium bicarbonate. In another embodiment, the coating solution contains from 2 wt. % to 3 wt. % sodium bicarbonate.

In an embodiment, the coating agent comprises a siloxane polyalkyleneoxide copolymer comprising ethyleneoxide. In an embodiment, the coating agent comprises a siloxane polyalkyleneoxide copolymer comprising octamethylcyclotetrasiloxane. In an embodiment, the coating agent comprises a siloxane polyalkyleneoxide copolymer comprising ethyleneoxide and octamethylcyclotetrasiloxane. In another embodiment, the coating solution contains from 2.5 wt. % to 3.5 wt. % siloxane polyalkyleneoxide copolymer.

According to another set of embodiments, the silicone septum comprising a surface coating as disclosed herein, is incorporated into an intravenous catheter assembly.

The catheter assembly may generally include a catheter coupled to a catheter adapter. In some embodiments, a catheter may be used in combination with a metallic introducer needle, as is commonly known and used in the art.

In some embodiments of the present invention, the coated septum, as disclosed herein, is positioned within a lumen of the catheter assembly to prevent or limit flow of a fluid through the catheter adapter. The coated septum generally includes a flexible or semi-flexible silicone material that is compatible with exposure to blood, medicaments, and other fluids commonly encountered during infusion procedures.

In some implementations of the present invention, a closed or partially closed pathway, such as a slit or small hole is further provided in a barrier surface of the septum. The pathway permits fluid to bypass the septum and flow though the catheter adapter. In some embodiments, the pathway is a slit that is closed prior to being opened or activated by a probe or septum activator positioned within the lumen of the catheter adapter. Prior to being opened or activated, the slit prevents passage of fluid through the catheter adapter.

Another general aspect of the disclosed invention relates to a method of reducing static charge among a plurality of vibrating silicone septa. The static charge may be reduced by coating the plural silicon septa according to the coating method disclosed herein.

It is to be understood that both the foregoing general description and the following detailed description are examples and explanatory and are not restrictive of the invention, as claimed. The various embodiments are not limited to the arrangements and instrumentality illustrated in the drawings. The embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawing in which.

DETAILED DESCRIPTION OF THE INVENTION

Figure 1:
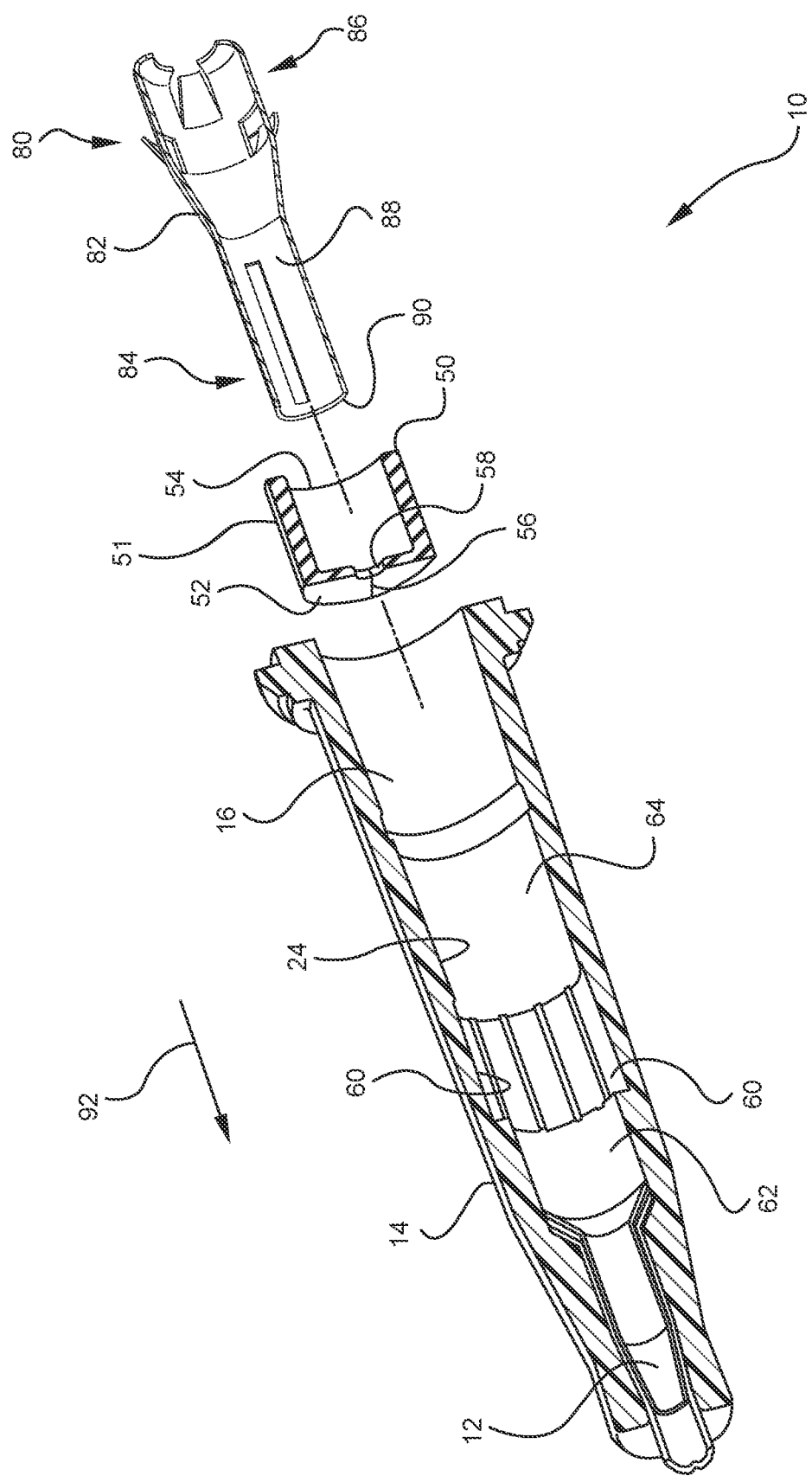
FIG. 1 is an exploded cross-sectional view of a coated silicone septum included within an intravenous catheter assembly.

The following description supplies specific details to provide a thorough understanding of the described coating for a silicone septum used in a vascular access device, such as an intravenous catheter assembly and the described method for coating a silicone septum. The following description further discloses an intravenous catheter assembly comprising a coated silicone septum. The following description also describes a method of reducing static charge among a plurality of vibrating silicone septa by coating the silicon septa as disclosed herein, thereby facilitating manufacture of intravenous catheter assemblies.

The skilled artisan would understand that the described silicon septum coating, vascular access device containing a coated septum, and related method for coating a silicone septum and method for reducing static charge of plural vibrating silicon septa are merely representative of presently preferred embodiments of the invention and that the details disclosed herein can be arranged and implemented in a wide variety of different configurations not limited to specific disclosed embodiments. Indeed, the disclosed coated silicon septum can be placed into practice by modifying the illustrated device and can be used in conjunction with any other apparatus and technique conventionally used in the industry.

The disclosed invention solves a problem observed during manufacture of an intravenous catheter assembly which includes a silicone septum, such as the Becton, Dickinson and Company Cathena® safety intravenous catheter assembly.

This silicone septum was originally coated with a Parylene coating to improve handling and manufacturing of the Cathena® safety intravenous catheter assembly. It was discovered that the Parylene coating degraded the performance of the catheter assembly. The Parylene coating was removed from the silicone septum. However, while designing the manufacturing equipment it was discovered that the un-coated septa were not able to achieve the required manufacturing feed rate through the vibrating bowl due to static charges created by the vibrating silicone septa within the vibrating bowl. The disclosed invention relates to two different silicon septum coatings shown to minimize the static charges during the vibrating cycles and improve the manufacturing feeding cycle rate.

In one embodiment, the silicone septum comprises a surface coating comprising a bicarbonate salt coating agent. The bicarbonate salt may be an alkali metal bicarbonate salt. Non-limiting examples of alkali metal bicarbonate salt include as lithium bicarbonate, sodium bicarbonate, and potassium bicarbonate.

In one embodiment, the silicone septum comprises a surface coating comprising a siloxane polyalkyleneoxide copolymer coating agent. The siloxane polyalkyleneoxide copolymer may include copolymer groups comprising ethyleneoxide, copolymer groups comprising octamethylcyclotetrasiloxane, or copolymer groups comprising ethyleneoxide and octamethylcyclotetrasiloxane. An example of this type of siloxane compound is SilwetR) L-8620 surfactant available from Momentive Performance Materials Inc.

The disclosed invention includes a method of coating a silicone septum. The method includes contacting an exterior surface of the silicone septum with a coating solution. The coating solution includes a solvent and a coating agent. The coating agent is selected from a bicarbonate salt and a siloxane polyalkyleneoxide copolymer. In one non-limiting embodiment, the solvent is water. The coating agent has a concentration in the solvent greater than 1 wt. %.

In the method, the exterior surface of the silicone septum is contacted with the coating solution for at least 5 minutes.

Excess coating solution is removed from the exterior surface of the silicone septum. The solvent is removed by drying, thereby leaving the coating agent deposited on the exterior surface of the silicone septum.

In one non-limiting embodiment, the coating agent may have a concentration in the solvent in the range from 1 wt. % to 10 wt. %. In another non-limiting embodiment, the coating agent has a concentration in the solvent in the range from 1 wt. % to 5 wt. %. In another non-limiting embodiment, the coating agent has a concentration in the solvent in the range from 2 wt. % to 4 wt. %.

In an embodiment, the coating agent comprises sodium bicarbonate. In another embodiment, the coating solution contains from 2 wt. % to 3 wt. % sodium bicarbonate.

In another embodiment, the coating solution contains from 2.5 wt. % to 3.5 wt. % siloxane polyalkyleneoxide copolymer. In an embodiment, the coating agent comprises a siloxane polyalkyleneoxide copolymer comprising ethyleneoxide. In an embodiment, the coating agent comprises a siloxane polyalkyleneoxide copolymer comprising octamethylcyclotetrasiloxane. In an embodiment, the coating agent comprises a siloxane polyalkyleneoxide copolymer comprising ethyleneoxide and octamethylcyclotetrasiloxane.

Other features and advantages of the present invention are apparent from the different examples that follow. The examples below illustrate different aspects and embodiments of the present invention and how to make and practice them. The examples do not limit the claimed invention.

Example 1. Coating and Deposition Methods for Siloxane Polyalkyleneoxide Copolymer Three percent by weight Silwet® L-8620 siloxane polyalkyleneoxide copolymer was mixed with distilled water to form a coating solution. This coating solution was mixed using mechanical mixer. Silwet® L-8620 siloxane polyalkyleneoxide copolymer is manufactured by Momentive Performance Materials Inc., Friendly, West Virginia. The copolymer comprises ethyleneoxide and octamethylcyclotetrasiloxane.

Plural silicone septa were dropped into a lube jar and shaken for 5 minutes on mechanical shaker with 100 RPM (Heidolph™ Vibramax Vibrating Platform Shakers, manufacturing No. 036130120).

The plural silicone septa were separated from the coating solution by pouring the mixture through a sieve (US standard size No. 6, Fisher scientific part No. 048841AB). The sieve pore size was 3.35 mm nominal sieve opening.

The plural silicone septa were left in the sieve and placed onto the shaker for 3 hours with 1100 RPM.

After shaking the septa to remove excess solution, the septa were left to dry overnight. The Silwet L-8620 siloxane polyalkyleneoxide copolymer coated septa were tested in the lab on a vibrating bowl which is similar to the production vibrating bowls. The concentration of the coating was confirmed in the lab. Thereafter the 3.0% Silwet L-8620 siloxane polyalkyleneoxide copolymer coated silicone septa were also tested on the manufacturing equipment. The empirical results showed that the Silwet L-8620 siloxane polyalkyleneoxide copolymer coated silicone septa met and exceeded the required manufacturing feed rates.

Example 2. Coating and Deposition Methods for Alkali Metal Bicarbonate

Two- and one-half percent by weight sodium bicarbonate was mixed with distilled water to form a coating solution. This coating solution was mixed using mechanical mixer.

Plural silicone septa were dropped into a lube jar and shaken for 5 minutes on mechanical shaker with 100 RPM (Heidolph™ Vibramax Vibrating Platform Shakers, manufacturing No. 036130120).

The plural silicone septa were separated from the coating solution by pouring the mixture through a sieve (US standard size No. 6, Fisher scientific part No. 048841AB). The sieve pore size was 3.35 mm nominal sieve opening.

The plural silicone septa were left in the sieve and placed onto the shaker for 3 hours with 1100 RPM.

After shaking the septa to remove excess solution, the septa were left to dry overnight. The sodium bicarbonate coated septa were tested in the lab on a vibrating bowl which is similar to the production vibrating bowls. The concentration of the sodium bicarbonate coating was confirmed in the lab. Thereafter, the 2.5% sodium bicarbonate coated silicone septa were also tested on the manufacturing equipment. The empirical results showed that the sodium bicarbonate coated silicone septa met and exceeded the required manufacturing feed rates. Some sodium bicarbonate crystals remained on the septa.

Another general aspect of the disclosed invention relates to a method of reducing static charge among a plurality of vibrating silicone septa. The static charge may be reduced by coating the plural silicon septa according to the coating method disclosed herein.

Another general aspect of the disclosed invention includes an intravenous catheter assembly comprising a coated silicone septum as disclosed herein.

A non-limiting example of a prior art catheter assembly is disclosed in U.S. Publication No. 2011/0160663A1, which disclosure is incorporated herein by reference. A non-limiting example of a commercially available catheter assembly is the Becton Dickinson and Company Cathena® safety intravenous catheter assembly.

Referring now to FIG. 1, an exploded, cross-sectional view of a catheter assembly 10 is shown. The catheter assembly 10 generally includes a catheter 12 coupled to a distal end of a catheter adapter 14. The catheter 12 and the catheter adapter 14 are integrally coupled such that an inner lumen 16 of the catheter adapter 14 is in fluid communication with a lumen 18 of the catheter 12. The catheter 12 generally comprises a biocompatible material having sufficient rigidity to withstand pressures associated with insertion of the catheter into a patient. In some embodiments, the catheter 12 comprises a rigid, polymer material, such as vinyl.

The catheter adapter 14 includes various design features and components to control and/or limit flow of fluid through the catheter assembly 10. For example, in some embodiments invention a septum 50 comprising a surface coating 51 as disclosed herein is positioned within the inner lumen 16 of the catheter adapter 14.

The septum 50 generally comprises a flexible, or semi-flexible polymer plug having an outer diameter that is configured to compatibly seat within a groove or channel 60 formed on an inner surface 24 of the catheter adapter 14. In some embodiments, the septum 50 is barrel shaped having a barrier surface 52 comprising a distal end of the septum 50 and further having an opening 54 comprising a proximal end of the septum 50. When positioned within the channel 60, the barrier surface 52 of the septum 50 divides the inner lumen 16 of the catheter adapter 14 into a forward fluid chamber 62 and a rearward fluid chamber 64. Thus, the presence of the septum 50 controls or limits passage of fluid between the forward and rearward fluid chambers 62 and 64. Specifically, a chosen configuration of the barrier surface 52 of the septum 50 largely determines the ability of a fluid to flow through the inner lumen 16 of the catheter adapter 14.

For example, in some embodiments the barrier surface 52 of the septum 50 is configured to include a slit 56. The slit 56 is configured to provide selective access or flow of a fluid through the barrier surface 52. In some embodiments, slit 56 is configured to remain in a closed, fluid-tight position until activated or opened by advancing a septum activator 80 through the slit 56 in a distal direction 92. In some embodiments, the barrier surface 52 comprises one slit 56. In other embodiments, the septum 50 can include more than one slit. In some embodiments, the septum consists essentially of a silicone rubber material.

Figure 2:
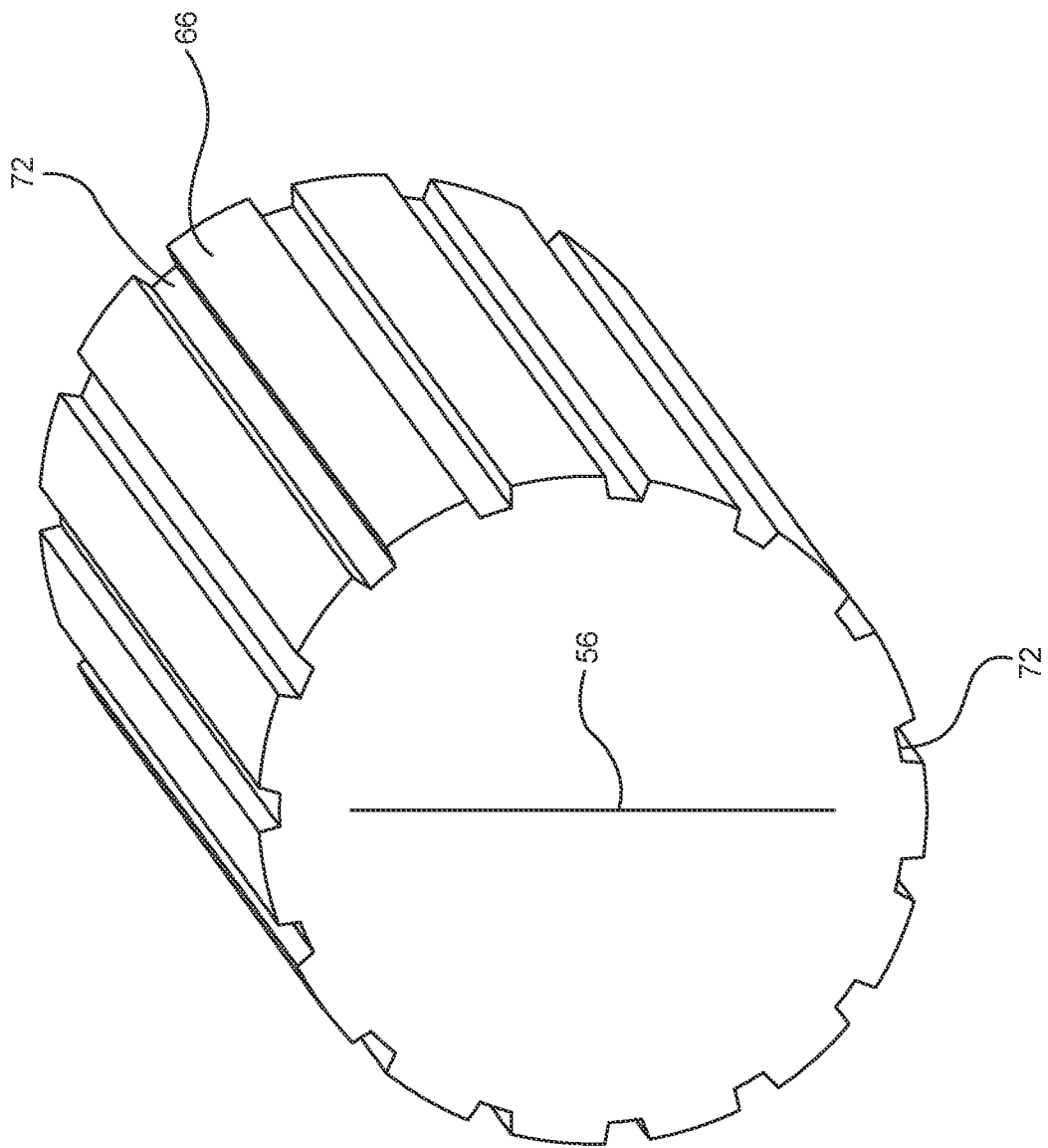
FIG. 2 is a perspective view of an embodiment of a septum in accordance with the disclosed invention.

Referring now to FIG. 2, an embodiment of a septum 150 is shown. The outer surface 66 of the septum 150 is provided with a surface coating as disclosed herein. In some embodiments, an outer surface 66 of the septum 150 is modified to include a plurality of recessed grooves 72. The recessed grooves 72 provide pathways between the forward and rearward chambers 62 and 64 through which air and/or fluid may flow. Thus, in some embodiments the outer surface 66 of the septum 150 is modified to provide desired flow between the forward and rearward chambers 62 and 64.

The features of the catheter assembly may be incorporated for use with an over-the-needle catheter assembly. For example, a flexible or semi-flexible polymer catheter may be used in combination with a rigid introducer needle to enable insertion of the catheter into a patient. Surgically implanted catheters may also be used.

Over-the-needle catheter assemblies are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter to facilitate insertion through the patient's skin into a blood vessel.

Following insertion of the catheter and introducer needle into the blood vessel at the catheterization site, the introducer needle is removed leaving the catheter in the blood vessel. Once inserted into a patient, the catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. The catheter 12 can be used for infusing fluid (e.g., saline solution, blood, medicaments, and/or total parenteral nutrition) into a patient, withdrawing fluids (e.g., blood) from a patient, and/or monitoring various parameters of the patient's vascular system. The removed introducer needle is considered a "blood-contaminated sharp" and must then be properly handled and discarded.

To increase safety, the intravenous catheter and needle assembly may be manufactured with a retractable needle. Some exemplary catheter and needle assemblies can comprise a hollow handle, a grip portion, a catheter hub comprising a catheter, and an elongate needle having a first position in which the elongate needle is slidably disposed within the catheter and a second position in which the elongate needle is slidably removed from the catheter and retracted at least in part into the hollow handle. As disclosed herein, the catheter hub can comprise a septum 50 configured to form a fluid-tight seal when the elongate needle is in the second position. The elongate needle passes through the septum when the elongate need is in the first position.

With continued reference to FIG. 1, the septum activator 80 comprises a probe-like structure that is primarily housed in the rearward chamber 64 of the catheter adapter 14. The septum activator 80 generally comprises a tubular body 82 having a distal end 84 and a proximal end 86. The tubular body 82 comprises a rigid or semi-rigid material. Such as a plastic or metallic material. The tubular body 82 further comprises an inner lumen 88 for facilitating flow of a fluid and/or liquid through the septum activator 80.

The distal end 84 of the tubular body 82 is configured to compatibly insert within the opening 54 of the septum 50. The distal end 84 further includes a probing surface 90 which extends through the opening 54 of the septum 50 to a position proximal to the barrier surface 52 of the septum 50. The probing surface 90 is advanced through the slit 56, or through the leak orifice 58 as the septum activator is advanced through the catheter adapter 14 in a distal direction 92.

It will be appreciated that the disclosed invention provides coatings for a silicone septum used with intravenous catheter assemblies. The disclosed invention further provides methods of coating a silicone septum. The silicone septum coatings disclosed herein may reduce static charge among a plurality of vibrating silicone septa to facilitate manufacture of intravenous catheter assemblies.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of coating a silicone septum comprising:
   contacting an exterior surface of the silicone septum with a coating solution comprising:
   a solvent; and
   a coating agent, wherein the coating agent is selected from a bicarbonate salt and a siloxane polyalkyleneoxide copolymer, and wherein the coating agent has a concentration in the solvent greater than 1 wt. %, wherein the exterior surface of the silicone septum is contacted with the coating solution for at least 5 minutes;
   removing excess coating solution from the exterior surface of the silicone septum; and
   drying the exterior surface of the silicone septum.

2. The method of coating a silicone septum according to claim 1, wherein the coating agent has a concentration in the solvent in the range from 1 wt. % to 10 wt. %.

3. The method of coating a silicone septum according to claim 1, wherein the coating agent has a concentration in the solvent in the range from 1 wt. % to 5 wt. %.

4. The method of coating a silicone septum according to claim 1, wherein the coating agent has a concentration in the solvent in the range from 2 wt. % to 4 wt. %.

5. The method of coating a silicone septum according to claim 1, wherein the solvent is water.

6. The method of coating a silicone septum according to claim 1, wherein the coating agent comprises sodium bicarbonate.

7. The method of coating a silicone septum according to claim 6, wherein the coating solution contains from 2 wt. % to 3 wt. % sodium bicarbonate.

8. The method of coating a silicone septum according to claim 1, wherein the coating agent comprises a siloxane polyalkyleneoxide copolymer comprising ethyleneoxide.

9. The method of coating a silicone septum according to claim 1, wherein the coating agent comprises a siloxane polyalkyleneoxide copolymer comprising octamethylcyclotetrasiloxane.

10. The method of coating a silicone septum according to claim 1, wherein the coating agent comprises a siloxane polyalkyleneoxide copolymer comprising ethyleneoxide and octamethylcyclotetrasiloxane.

11. The method of coating a silicone septum according to claim 10, wherein the coating solution contains from 2.5 wt. % to 3.5 wt. % siloxane polyalkyleneoxide copolymer.

12. A method of reducing static charge among a plurality of vibrating silicone septa, comprising coating the silicon septa according to the method of claim 1.

13. A method of reducing static charge among a plurality of vibrating silicone septa, comprising coating the silicon septa according to the method of claim 4.

* * * * *